United States Patent [19]

Breithbarth

[11] Patent Number: 5,785,977
[45] Date of Patent: Jul. 28, 1998

[54] NON-METALLIC MICROPARTICLE CARRIER MATERIALS

[76] Inventor: Richard Breithbarth, 17 Baird Pl., Whippany, N.J. 07981

[21] Appl. No.: 597,972

[22] Filed: Feb. 7, 1996

[51] Int. Cl.$^6$ ............................................. A61K 6/90
[52] U.S. Cl. ........................ 424/401; 524/801; 524/837
[58] Field of Search ........................ 424/401; 524/801, 524/837

[56] References Cited

U.S. PATENT DOCUMENTS

| | | | |
|---|---|---|---|
| 4,824,890 | 4/1989 | Glover et al. | 524/253 |
| 4,935,464 | 6/1990 | Ona et al. | 524/837 |
| 4,999,398 | 3/1991 | Gravier et al. | 524/837 |
| 5,371,139 | 12/1994 | Yokoyama et al. | 524/837 |
| 5,504,149 | 4/1996 | Kosal | 524/837 |
| 5,643,555 | 7/1997 | Collin et al. | 424/59 |

*Primary Examiner*—Terressa Mosley
*Attorney, Agent, or Firm*—Evelyn M. Sommer

[57] ABSTRACT

Non-metallic microparticulate carrier materials for a large and varied group of pharmaceutical and cosmetic agents are disclosed. Microdispersions of such carrier materials charged with at least one such pharmaceutical and/or cosmetic agent are also described. The microdispersions can be formulated for oral, parenteral, topical, inhalation and suppository administration. The formulations have varied uses depending on the pharmaceutical and or cosmetic agent utilized such as for combating microbial, fungal, yeast, viral and the like infections, treating acne, Herpes, burns, dermatoses caused by poisonous plants and irritants, reduction of wrinkles, moisturizing skin, etc. The microparticles are suitably charged particles of silica, alumina, boron, charcoal and the like and have a particle size of about 3 to about 250 μm. The pharmaceutical and cosmetic active materials, which include ozone, vitamins, hormones, steroids, minerals humectants, etc., complex with the microparticles. The liquid carrier for the microparticles include water, propylene glycol, alcohols such as methanol, ethanol and propanols, and dimethyl sulfoxide. The resulting dispersions are believed to be similar to isotonic saline and mimic body fluids which makes the dispersions very physiologically compatible thereby aiding and speeding the delivery of the agents across membranes and to the afflicted tissue. Methods of using these microdispersions and the containing the same are also disclosed.

14 Claims, No Drawings

NON-METALLIC MICROPARTICLE CARRIER MATERIALS

The present invention is directed to non-metallic microparticle carrier materials for a large and varied group of pharmaceutical and cosmetic agents. More particularly, the invention is directed to non-metallic microparticles, the electrical surface charge of which has been adjusted so that they can serve as carrying agents for a large and varied group of pharmaceutical and cosmetic agents, the resultant products and methods of making and using these microparticulate materials. Still more particularly this invention involves microdispersions of non-metallic microparticles having affixed to their surfaces by charge bonding at least one therapeutically and/or cosmetically valuable material, which microdispersions remain stable for long periods of time and which are useful for therapeutic and cosmetic purposes by humans and animals.

According to the invention, there are provided novel compositions of non-metallic microparticles carrying on their surface a pharmaceutically active or a cosmetic agent. The invention, in addition provides pharmaceutical and cosmetic compositions containing the above novel materials and a pharmaceutically acceptable carrier therefore. In the preferred embodiments of the invention, the pharmaceutical or cosmetic composition is comprised of a composition of the invention in stable microdispersion form suitable for injection, topical application or oral ingestion.

The invention further provides novel methods of treatment and prevention of a wide variety of medical conditions in humans and other mammals.

Depending on the pharmaceutically active agent carried by the microparticulates, application of compositions of the present invention are believed to be effective against a wide range of medical conditions. These conditions include, but are not limited to, use in treating: acne; dermatitis; bacterial infections; fungal infections; yeast infections; agents for ameliorating the severity of burns, anti-fungal agents, anti-yeast agents, anti-viral agents, anti-inflammatory agents, psychotropic agents such as serotonin, diazines such as silver sulfurdiazine, anti-infective agents, skin ulcer healing agents, agents for treating skin irritation, agents for minimizing the extent and severity of Herpes Simplex, genital herpes and chicken pox lesions, agents for treating acne infected skin, moisturizing agents, wrinkle reducing agents, electrolyte replacement agents, viral infections, including those of the herpes type such as herpes simplex, chicken pox (herpes zoster), and genital herpes; the treatment of insect and animal stings and dermatoses caused by poisonous plants and other irritants and allergens; and treatment of indolent neoplasms of the skin, such as warts or moles. It is also useful as an anti-pruritic, in alleviating the symptoms of burns, and in preventing the transmission of STDs, including HIV (Human Immunodeficiency Virus) infection. Systemic injections of compositions of the present invention are further believed to be effective in the treatment of systemic viral, bacterial, fungal and yeast infections, swollen joints, and other conditions.

Binding ozone or nascent oxygen to the microparticulate material results in compositions having enhanced activity against microorganisms including staphylococcus, streptococcus, pseudomonas, enteric bacteria, molds, yeast, selected viruses, trichomonas, actinomyces and bacteroides.

The novel compositions can be applied topically, parenterally or taken orally, rectally or vaginally depending on the active agent and its intended purpose. Moreover, it is now believed that the activity of the pharmaceutical agent is significantly enhanced so that materials that are normally effective only at toxic levels can now be administered at subtoxic levels and still be effective.

Topical application of the novel compositions are believed to be effective in the treatment of muscular aches and pains (methyl salicylate), arthritic conditions (salicylates, hyaluronic acid, etc), dermatological fungicides, ($\alpha$-hydroxy fruit acids, humectants, Vitamin A, Vitamin D, fungicides, Vitamin E, etc), topically and orally as germicides, fungicides, hormones, a source of hormonally active materials, minerals, vitamins, steroids, pain relieving agents, enzymes, etc., parenterally to provide electrolytes, antibiotics, anti-infectives, agents for ameliorating the severity of burns, anti-yeast agents, anti-viral agents, anti-inflammatory agents, agents for treating skin irritation, agents for minimizing the extent and severity of Herpes Simplex, genital herpes and chicken pox lesions, agents for treating acne infected skin, moisturizing agents, wrinkle reducing agents and electrolyte replacement agents, etc.

Still further, the compositions can be formulated into lotions, creams, foams and the like for use in sunscreens and other skin care and cosmetic products including anti-aging and anti-wrinkling products.

In accordance with other embodiments of the invention, therapeutic agents that at present are administered parenterally, i.e., intravenously, intraperitoneally, and intramuscularly, can be converted into orally administered preparations. For example, parenteral forms of electrolytes, antibiotics, anti-virals, etc., can, using the microparticles of the invention, now be formulated for oral ingestion.

The pharmaceutical or cosmetic agent is, in accordance with the invention, complexed with a non-metallic microparticle, the surface of which microparticle is able to complex with the agent by ionic bonding. The success of utilizing such solid particles, depends largely on several key factors. The qualities of the ideal particles (matrix materials) are dependent on their very small, size, electrical potential, zeta potential, uniformity, spherical shape and rigid nature and their good flow properties. The particles should possess a supply of chemical groups, especially anionic groups, and thereby bond ionically to a variety of agents, especially agents with cationic groups. Moreover, the particles should be chemically stable to the conditions of coupling, adsorption and elution. Until recently, almost all matrix materials have been derivatives of cellulose, polystyrene or synthetic poly-amino acids, cross-linked dextrans, polyacrylamide gels and agarose. Although these insoluble non-metallic carriers are a diverse group, certain restrictions limit their usefulness to specific situations, e.g., cellulose's usefulness is limited by its fibrous and non-uniform character which impedes proper penetration of large molecules. Polystyrene, polyacrylamide and cross-linked dextran gels have low porosity. The beaded derivatives of agarose are ideal for use in some situations. The beads are uniform, small, stable and spherical and have a high capacity for substitution. However, the usefulness of these beads is limited by their temperature lability and by their tendency to break down.

The carriers preferred for use herein include silica, charcoal, alumina and boron microparticles.

Microparticles derived from silica and boron materials are the preferred, and most widely used, microparticles. The silica materials are available commercially as porous granules of high quality, silica permeated by interconnecting pores of uniform and precisely controlled sizes. While such materials are insoluble and largely unaffected by changes in their immediate environment, pH and ionic strength changes may affect the microparticles charge, and thus its ability to bind the desired agents. It is preferred that the microparticles have a substantial negative charge at physiological pH and physiological ionic strength. The microparticles of the present invention are also resistant to microbial attack and can be sterilized by disinfectants or heating. The surface of useful silica particles usually provides a plurality of hydroxyl groups which exhibit a negative charge in aqueous solution.

Silica particles are available in at least two types, macroparticulate and microparticulate. The macroparticulate silica particles typically have a mean particle diameter greater than about 250 μm and are rather porous. The microparticulate silica particles typically used herein have a mean diameter of greater than about 3 μm and are also usually porous. Desirably these microparticles have a mean diameter of less than about 100 μm, more desirably less than about 14 μm, and more desirably less than about 10 μm. Useful silica microparticles usually also have either spherical or moderately irregular shapes. Microparticulate silica particles display the highest efficiencies as well as the greatest loading capacity. The silica particles can be used directly or modified by coating or chemically bonding an active phase onto the silica particle's surface.

Alumina (aluminum oxide) $Al_2O_3$ particles are also suitable for use herein, even though aluminum is a metal. Alumina occurs in nature and is a white crystalline very hard powder that is insoluble in water, but which displays non-metallic properties even though it comprises a metal (thus, for the purposes of this disclosure, a material is nonmetallic if its properties are nonmetallic even if it comprises one or more metallic ions). When activated, it can be used for attachment of other molecules. Alumina microparticles have an average particle size of about 7 μm.

Similarly to alumina, charcoal (such as that sold under the trade name Darco) is a water insoluble nonmetallic microparticulate material that can be used for attachment of other molecules.

Boron compounds, such as boric acid, sodium borohydride, boric anhydride and sodium borate can also be used effectively.

The particle sizes for silica described herein are useful as guidelines for selecting particle sizes for other microparticulate materials that are useful in the present invention.

The choice of microparticulate material is dependent on the specific conditions that may be unique for each application. However silica microparticles are preferred.

The particles may already carry the desired electrical charge or they can be modified using the conventional techniques so that they exhibit the appropriate charge. Such techniques include exposure to corona discharge, high shear intense grinding and chemical treatment.

The bonding capacity of the particles may be further increased by applying to the particles' surfaces a surfactant coating, for example a Tween (such as TWEEN 20 (polyoxyethylenesorbitan monolaurate, CAS Registry number 9005-64-5) or TWEEN 80 (polyoxyethylenesorbitan monooleate, CAS Registry number 9005-65-6)), an alkyl-benzene sulfonate, polyethylene glycol, ethoxypolyethylene glycol or an oxyethylenated glycol surfactant. Desirably the surfactant is a Tween.

The composition of the present invention can be applied as a liquid using water or propylene glycol as the carrier, or it may be in the form of a gel, cream, liquid or spray. Additionally, the composition of the present invention may be adapted for parenteral, topical, oral, nasal, vaginal or suppository administration.

In the preparation of the ozonated microparticles, the ozone gas can be passed through a vessel containing the microparticles dispersed in an aqueous medium, under conditions that provide for intimate contact between the microparticulate starting material and the ozone. For example, thin film procedures, sparging, gas entrainment procedures, and the like. On a small scale, for example, the microparticles can be placed in a vented vessel, and ozone is sparged through the material until the reaction is complete. The ozone may advantageously be generated with any of the commercially available ozone generators. Such devices include corona discharge tubes through which oxygen gas may be passed. For instance, passing pure oxygen gas through an ozone generator will typically leave the device as from 2% to 6% $O_3$ (ozone), with the remainder $O_2$. This ozone mixture may then be sparged through the microparticles at ambient temperature and pressure until the reaction is complete.

Completion may be judged by analyzing the gas exiting the ozonation chamber for ozone. (This may be done by passing the exit gas through aqueous potassium iodide and determining whether iodine gas is liberated, or by any other conventional technique). Alternatively, the reaction may be followed by observing the weight gain of the material undergoing the reaction, or by calculating the quantity of ozone needed to fully ozonate the material and stopping the reaction when a slight excess of ozone has passed through the reaction chamber. Because the reaction is exothermic, its progress may also be followed by monitoring the heat evolved and stopping the flow of ozone when the mixture ceases to generate heat.

The ozone can be utilized in admixture with oxygen or air, the admixture preferably containing about 0.1 and 15 mole percent ozone. The heart of the invention, in the case, of the ozonated microparticles lies in the continuous and lengthy release of oxygen from the microparticles.

It is desired that the pharmaceutical or cosmetic agent, for instance, vitamin C and shark cartiledge is in a form that carries a positive charge and is of a particle size less than 100 μm.

If the microparticles are to have a coating applied to them, the microparticles are introduced into a vessel containing water and which has been provided with a high shear mixer. A surfactant, desirable a food grade surfactant if the final preparation is to be taken orally, is then introduced and the resultant mixture subjected to strong agitation. The active agent pharmaceutical and/or cosmetic can be directly introduced into this same mixing vessel when the coating operation is complete and the agitation continued for forming the final product.

The surfactant is preferably added in an amount from about 10 to about 15% by weight wherein a total of 100% by weight of the composition is obtained and preferably in a range of about 3 to about 10% by weight of the total composition in the mixing vessel.

As already noted, the active agent bound to the microparticles can be:
1. ozone;
2. a hormone such as thyroxin, progesterone and the like;
3. a mineral such as zinc sulfate, calcium carbonate, calcium phosphate and the like;
4. a vitamin such as Vitamin A (ascorbic acid), Vitamin E, ascorbyl palmitate B6, B12 and the like;
5. an anitoxidant, or admixture of antioxidants, such as Citrus Bioflavonoids, N-acetyl Cysteine, CoQ10, L-cystenine, L-glutathione, Grape extract with procyanadins, green teal extract with catechins, ginko bilobo extract with flavoneglycosides, garlic with allicin, Vitamin C, Vitamin E and β-carotene;

6. a nutritional supplement containing one or more of the following: vitamin a, vitamin c, vitamin e, vitamin b1, vitamin b2, thiamine, niacin, vitamin b6, folic acid, vitamin b12, biotin, pantothenic acid, choline, inositol, para amino benzoic acid, dimethyl glycine, vitamin d, chromium, calcium, iron, iodine, magnesium, zinc, selenium, copper, manganese, potassium, phosphorous, boron, molybdenum, silicone, vanadium, bromelin, papain, amylase, protease, lipase, cellulase, L-leucine, L-valine, L-isoleucine, L-alanine, L-glutamine, L-tyrosine, L-taurine, L-glycine, L-aspartic, L-carnitine, L-lysine, L-methionine, Siberian ginseng root, Chinese astragalus root, licorice root, Ginkgo Biloba leaf, Codonopsis root, Fo Ti root, wild American ginseng root, kirin Chinese red ginseng root, Korean white ginseng root, valerian extract, oat straw extract, passionflower extract, mild thistle extract, hops flower, skullcap herb, chamomile flower, shattered cell wall Chlorella, wheat grass, barley grass, wheat germ, alfalfa leaf, suma, blue green algae, lecithin, ginger root, red raspberry leaf, peppermint leaf, capsicum fruit, and vanilla; and 7. a pharmaceutical or cosmetic agent such as procaine hydrochloride, a steroid, coenzyme $Q_{10}$, methyl salicylate, hyaluronic acid, µL-hydroxy fruit acids, Vitamin A & D derivatives, including limonene, panthenol, a terpene, β-carotene, geraniol, psychotropic agents such as serotonin, catnip, peppermint, rosemary, rue, vervain, wood betony, holy thistle and skullcap, ginko bilobo and the like.

In one preferred embodiment of the present invention, the compositions of the present invention are formulated into pharmaceutical preparations. These pharmaceutical preparations include one or more of the microparticulate active compositions of the present invention, and may further include other pharmaceutically active ingredients.

In addition, any of the well-known pharmaceutically acceptable carriers, excipients and/or diluents may be combined with the compositions of the present invention in a well known manner. Suitable diluents include, for example, water, polyethylene glycol, isopropyl myristate, magnesium stearate, calcium stearate, magnesium carbonate, calcium carbonate, magnesium silicate and mineral oil. The pharmaceutical composition may be in any form suitable for topical use, such as an ointment, gel, or cream. Conventional coloring, fragrance and preserving agents may also be provided.

The effective dosage of the compositions of the present invention is believed to be much lower than would be expected in light of the prior art, suggesting that the agents have unexpectedly high efficacy in this form. While the compositions may be used neat (and, indeed, some of them form pharmaceutically elegant creams or ointments), the effective concentration for most topical applications can be as little as 0.01%, by weight. However, the compositions preferably contain from about 0.5% to about 20%, more preferably from about 1% to about 10%, by weight active ingredient. Topical compositions containing about 2% to about 3% of active ingredient appear to be particularly effective.

For systemic use, such as intravenous, intramuscular, or intraperitoneal injection, the compositions may similarly contain from about 0.01% to about 99% active ingredient, by weight. Preferred systemic compositions contain from about 0.05% to about 20% active ingredient, by weight.

The effective dosage of the compositions of the invention, when administered orally, must take into consideration the diluent, preferably water and the intended purpose sought to be achieved. The compositions preferably contain 0.05% to about 75% by weight active microparticles and preferably about 0.1% to about 50% by weight. When the compositions are ingested, desirably they are taken on an empty stomach.

The present invention is also suitable for systemic and localized injection of the compositions disclosed herein, including intravascular, intramuscular, subcutaneous, intraperitoneal, and other injection techniques. Such injection may be used for treatment of viral, fungal and bacterial infection.

Pharmaceutical compositions of the present invention can also be administered as an aerosol, for example, as a spray or nebulizer solution, or as a suppository. In such cases, the inventive microparticle-agent complexes are combined with the conventional other components for the corresponding means of administering the agent. There is no evidence that the microparticles of the present invention are toxic in topical, systemic and oral use at the levels described herein.

As noted above, the compositions of the invention, i.e., the microparticles suitably loaded with an appropriate pharmaceutical agent are effective for treatment of bacterial, viral, and fungal infections. Such compositions are also believed to be effective to minimize the extent and severity of Herpes Simplex, genital Herpes and chicken pox lesions when applied on incipient eruptions.

Additionally, these compositions are believed to be effective in treating fungal infections on the skin and nails, such as athlete's foot and oxychomycosis and to have a shrinking effect on warts and moles. Moreover, our data further indicate that topical application of the microparticles of the present invention, after significant exposure to the ultraviolet component of sunlight, is effective in ameliorating the severity of sunburn and facilitating the healing process. Similar reduction of pain, inflammation, and blistering, and an increase in the speed of the healing process has been observed when the composition of the present invention is applied to first and second degree thermal burns on a mammal.

A preferred method of producing the basic compositions comprises the following steps: water or other suitable diluent and, desirably, a surfactant, for example TWEEN 20 (polyoxyethylenesorbitan monolaurate, CAS Registry number 9005-64-5) or 80 (polyoxyethylenesorbitan monooleate, CAS Registry number 9005-65-6)), are continuously stirred in a mixing vessel provided with a homogenizer (a high shear mixer such as a Greerco). The microparticles having a suitable surface charge are then added, preferably ionically charged silica particles having a particle size of about 3 to 10 µm in an amount of preferably 7.5 to 20% by weight and most preferably 10–15% by weight. The active agent is then added so that a final concentration of a pharmaceutical amount of active agent will be realized and the resultant mixture stirred at high speed to form a stable microdispersion of all of the components. The compositions (microdispersions) can also include a suitable buffer, a preservative, a coloring agent, flavoring agent or any other conventional adjuvants for the intended mode of application and end use.

The following examples are give in order to more completely illustrate the invention, but are not to be construed as limiting the scope thereof.

EXAMPLE 1

Silica microparticles having a negative charge and a particle size of about 3 to about 5 µm are introduced into a mixing vessel filled with about 1000 ml distilled water.

Production of the ozone-oxygen mixture is obtained by following the specifications for production or bottling of medical oxygen. The ozone is formed by silent electric discharge (absolutely nitrogen-free, to avoid the formation of aggressive and reactant nitrogen oxides, especially radicals). For ozonization microparticles are treated with a continuous run through of concentration which is used is preferably in the range of fifty to seventy micrograms per milliliter. The bubbling through of the aqueous dispersion under thermostat setting at about 20 degrees C. A continuous flow through is important, a uniform bubbling time of 180 to 300 minutes is required depending on the specific ozone concentration of the ozone-oxygen discharge mixture.

EXAMPLE 2

Example 1 is repeated using negatively charged alumina microparticles having a particle size of about 5–10 μm.

EXAMPLE 3

Silica microparticles having a particle size of about 3 to about 10 μm, and a negative surface charge are introduced into a Greerco mixer containing 88% water and 12% TWEEN 20 (polyoxyethylenesorbitan monolaurate, CAS Registry number 9005-64-5). The microparticles are present in an amount of 14% by weight. After intensive stirring of this mixture for 25–35 minutes, Vitamin A, 1% by weight, and Vitamin E, 1% by weight, are added to form a stable microdispersion.

EXAMPLE 4

Example 3 is repeated using α-hydroxy fruit acids, 1.5% by weight, instead of the Vitamins A and E.

EXAMPLE 5

A topical cream for acne is prepared utilizing ozonated silica microparticles prepared as described above.

2.5% w/v ozonated microparticles of silica having a particle size of 5–7 μm;
48% w/v propylene glycol,
30% w/v propylparaben;
5% w/v polysorbate 60;
10% w/v glycerol monostearate; and
balance mineral oil.

The preparation is believed to be non-irritating to acne infected skin and to have a strong anti-comedonal effect when used topically on affected areas. It is believed these compositions deliver nascent oxygen to kill anaerobic bacteria such as P. acne.

In a separate preparation, it is believed that benzoyl peroxide can be combined with the other components to produce equally good results.

EXAMPLE 6

A topical gel effective against burns is prepared as follows:

10% w/v silica microparticles having a particle size of 3–5 μm;
1% w/v aloe vera gel applied onto the silica microparticles;
60% w/v carbomer 934;
1% w/v disodium edetate;
10% w/v glycerin; and
balance propylene glycol MW 400.

This composition is applied topically to only a portion of the skin surface of a severely sunburned patient in a single application within two hours after exposure to sunlight. The treated area is believed to heal better than the untreated areas.

EXAMPLE 7

An injectable composition effective against fungal infections is prepared as follows:

25 mg/ml clotimazole is applied onto TWEEN 20 (polyoxyethylenesorbitan monolaurate, CAS Registry number 9005-64-5) coated silica particles having a negative charge. The silica particles have a particle size range of about 3 to about 5 μm. These coated particles are then suspended in polyethylene glycol MW 200.

EXAMPLE 8

An injectable composition for treatment of swollen joints is prepared using silica microparticles having a slight negative charge and a particle size of less than 5 μm.

A cortico steroidal medication, 25% by weight, is applied to the silica and the product is suspended in polyethylene glycol MW 200.

Patients at a sports medicine clinic complaining of swollen knees are given an injection (0.1 mg./kg) of this composition into the swollen knee. It is believed that the injection reduces swelling in the knees without inflammatory reactions.

This example is repeated using surfactant coated particles and producing, it is believed, substantially the same results.

EXAMPLE 9

A topical spray to prevent infections from superficial cuts, scrapes and bruises and as a home remedy for minor infections for the treatment of scratches, scrapes, cuts and punctures of the human skin is prepared from:

1% w/v of benzocaine applied onto the microparticles of Example 1;
2.5% w/v of methanol;
10% w/v of aloe vera oil; and
balance water.

The composition is believed to be particularly effective and indicated to avoid staph aureus infections.

EXAMPLE 10

An ingestible composition is prepared by dispersing 2.5 gm of negatively charged silica particles having a mean particle diameter of less than 8 μm in 22.5 ml of water. Once the dispersion is formed, 500 units of vitamin C are added and the admixture is sonicated until a stable composition is formed. This composition is believed to be effective in treating the common cold.

EXAMPLE 11

An ingestible composition is prepared by suspending 40 gm of sodium borate with a mean particle diameter of less than 10 μm and 1000 units of shark cartiledge powder in 250 ml of deionized water. A 25 ml dosage of this suspension on a daily basis is believed to be effective in ameliorating cancer.

What I claim is:

1. A stable dispersion of non-metallic microparticles having a particle size of about 3 to about 250 μm, said microparticles being adapted for uses selected from the group consisting of pharmaceutical and cosmetic uses and carrying a negative surface charge, in a liquid carrier selected from the group consisting of water, methanol, ethanol, propanol, dimethyl sulfoxide, polyethylene glycol and mineral oil.

2. A stable dispersion according to claim 1 wherein said microparticles have a particle size of about 3 to about 14 μm.

3. A stable dispersion according to claim 1 wherein said microparticles are selected from the group consisting of silica, alumina, boron, and charcoal particles.

4. A stable dispersion according to claim 1 wherein said microparticles are selected from the group consisting of silica and alumina microparticles.

5. A stable dispersion according to claim 1 wherein said microparticles are silica microparticles.

6. A stable dispersion according to claim 1 wherein said liquid carrier is water.

7. A stable dispersion according to claim 1 wherein said liquid carrier is propylene glycol.

8. A stable dispersion according to claim 1 further comprising a surfactant.

9. A stable dispersion according to claim 8 wherein said surfactant is a member selected from the group consisting of polyoxyethylenesorbitan monolaurate, polyoxyethylenesorbitan monooleate, alkylbenzene sulfonates, polyethylene glycols, ethoxylpolyethylene glycols and oxyethylenated glycols.

10. A stable dispersion according to claim 8 wherein said surfactant is a member selected from the group consisting of polyoxyethylenesorbitan monolaurate and polyoxyethylenesorbitan monooleate.

11. A stable dispersion according to claim 1 wherein said non-metallic microparticles are complexed with an agent selected from the group consisting of pharmaceutical and cosmetic agents.

12. A stable dispersion according to claim 1 wherein said microparticles are selected from the group consisting of alumina, boron, and charcoal particles.

13. A stable dispersion according to claim 1 wherein said microparticles are alumina microparticles.

14. A stable dispersion according to claim 1 wherein said microparticles are boron microparticles.

* * * * *